United States Patent [19]

Watt

[11] Patent Number: 4,600,462
[45] Date of Patent: Jul. 15, 1986

[54] INCORPORATION OF A HYDROPHILE IN FIBROUS WEBS TO ENHANCE ABSORBENCY

[75] Inventor: William R. Watt, Princeton Junction, N.J.

[73] Assignee: James River/Dixie-Northern, Inc., Norwalk, Conn.

[21] Appl. No.: 724,058

[22] Filed: Apr. 18, 1985

Related U.S. Application Data

[60] Continuation of Ser. No. 482,794, Apr. 7, 1983, abandoned, which is a division of Ser. No. 306,718, Sep. 29, 1981, abandoned.

[51] Int. Cl.⁴ .............................................. B32B 31/00
[52] U.S. Cl. .................................. 156/278; 156/296; 427/386; 427/389.9; 428/913; 428/288; 604/368; 604/372; 604/376
[58] Field of Search ................ 427/385.5, 386, 389.9, 427/391, 392; 604/368, 372, 376; 428/913; 156/62.6, 278, 296

[56] References Cited

U.S. PATENT DOCUMENTS

| | | | |
|---|---|---|---|
| 3,617,439 | 11/1971 | Chapman | 162/179 |
| 3,664,343 | 5/1972 | Assarsson | 162/168 R |
| 3,674,632 | 7/1972 | Wennergren | 162/168 |
| 3,686,024 | 8/1972 | Nankee et al. | 162/168 R |
| 3,808,165 | 4/1974 | Duchane | 428/913 |
| 4,008,353 | 2/1977 | Gross et al. | 428/913 |
| 4,096,311 | 6/1978 | Pietreniak | 428/289 |
| 4,105,033 | 8/1978 | Chatterjee et al. | 162/177 |
| 4,145,248 | 3/1979 | Van Fenson | 162/168 R |
| 4,154,647 | 5/1979 | Rowe | 162/157 R |
| 4,156,628 | 5/1979 | Rowe | 162/157 R |
| 4,292,105 | 9/1981 | Taylor | 427/389.9 |
| 4,309,469 | 1/1982 | Varona | 428/913 |
| 4,362,781 | 12/1982 | Anderson | 428/913 |
| 4,392,861 | 7/1983 | Butterworth et al. | 428/290 |

Primary Examiner—James J. Bell
Attorney, Agent, or Firm—Finnegan, Henderson, Farabow, Garrett & Dunner

[57] ABSTRACT

An air laid fibrous web product of enhanced absorbency and method of making same having a basis weight of between about 8 to about 50 pounds per ream, and a bulk of at least 0.40 mils per pound per ream, the web product comprising a multiplicity of papermaking fibers distributed randomly in the form of a web, an adhesive material, preferably a latex, essentially permeating said web of randomly distributed fibers and upon curing bonding adjacent fibers, the adhesive material representing between about 15 to about 30% of the basis weight of the web product and between about 0.1 to about 5.0 by weight of a hydrophile, said hydrophile substantially coating the bonded fibers. The hydrophile is applied to the web as an aqueous solution downstream of the bonding station, either in an immersion or spray treating step.

14 Claims, 2 Drawing Figures

⊙ IMMERSION METHOD
△ SPRAY METHOD

INCORPORATION OF A HYDROPHILE IN FIBROUS WEBS TO ENHANCE ABSORBENCY

This application is a continuation of application Ser. No. 482,794, filed Apr. 7, 1983, now abandoned, which is a division of application Ser. No. 306,718, filed Sept. 29, 1981, now abandoned.

FIELD OF INVENTION

The present invention relates to air laid (or dry laid) fibrous webs of enhanced absorbency rate. More specifically, the invention relates to air laid cellulosic webs whose individual fibers are bonded together by a hydrophobic adhesive binder material essentially permeating said web, a hydrophile being incorporated within the web matrix to facilitate absorption of moisture. Most specifically, the invention relates to tissue, towel and napkin products of high bulk and absorbency obtained from air laid cellulosic fibrous bonded webs, the fibrous webs containing less than about 5% by weight of a hydrophile, the inclusion of the hydrophile substantially reducing the inherent water repellancy of the hydrophobic binder.

BACKGROUND OF INVENTION

Fibrous webs, particularly low basis weight webs between 8 and 50 lbs. per ream (3,000 sq. ft.), for use ultimately as tissue, towel and napkin products, are fabricated conventionally by two alternate processes. The older wet laid process dispenses an aqueous slurry of pulped paper-making fibers, typically natural cellulose fibers, from a headbox onto a moving foraminous support means, e.g., a fourdrinier wire, the aqueous medium being removed through the support means by vacuum means. The wet laid web is thermally dried and taken up on a parent roll. Because of the presence of water, the wet laid web fibers bond naturally to one another by means of hydrogen bonding. Furthermore, the high water content of the wet laid web, which decreases from about 99% by weight beneath the headbox to between about 35 to 50% just prior to consolidation, facilitates densification of the web. The water "lubricates" the web so that the individual fibers can come into close physical relationship with one another. The result is a densified web of low bulk, but having good absorbency.

The second, now conventional, yet relatively recent, process defiberizes cellulose pulp, the dry individual fibers being pneumatically transported to the dispensing means, and then dry laid (or air laid) onto the moving foraminous support means. Vacuum means below the support means is employed to ensure that the dry fibers remain in the web, which web has little inherent strength inasmuch as hydrogen bonds are not formed in the absence of an aqueous medium. The dry, initially laid web is then sprayed with a synthetic bonding agent, such as a latex emulsion, preferably on both surfaces of the web. The bonding agent is cured by passing the thus treated web though a dryer, e.g., a through air dryer, before being taken up on a parent roll.

The bonding agent characteristically is a hydrophobic substance, that is antagonistic to water, and of limited solubility in water. The bonding agent permeates the web, and encapsulates a major portion of the otherwise hydrophilic fibers. Notwithstanding the thus diminished absorbency capabilities of dry laid webs, these products have certain advantageous properties. The high bulk reduces the amount of fiber per ream (3000 sq. ft.) of paper product, and the presence of the bonding material increases wet strength, making these products particularly useful as industrial or heavy duty wipes. The dry laid process also permits better formation of the fibrous matrix, thereby improving softness and aesthetic appeal. Thus, it is apparent that dry laid products have a distinct absorbency disadvantage as compared to their wet laid counterparts even though superior in other aspects.

SUMMARY OF THE INVENTION

It is an object of the present invention to provide a method for manufacture of an air laid fibrous web product of enhanced absorbency rate.

It is another object of the invention to provide a method for manufacture of a bulky, absorbent cellulosic web product having a high degree of perceived softness.

It is a further object of the invention to provide a method for the manufacture of an air laid fibrous web product whose individual fibers are bonded together by a hydrophobic adhesive binder material, the web also containing a hydrophile to promote absorbency by reducing substantially the water repelling effects of the binding material. Advantageously, the incorporation of the hydrophile does not reduce the bulk, nor appreciably affect the wet tensile properties of the product.

These and other advantages and objects of the invention will be readily perceived upon inspection of the drawings, and upon a reading of the detailed description of the invention, a summary of which follows.

The method of the present invention contemplates the incorporation of a hydrophile by immersion or spray means simultaneous with, or preferably subsequent to, the application of binding agent to the web. The hydrophile is dissolved in an aqueous solution which contains between about 0.1 to 10.0% by weight of the hydrophile. While the concentration is not critical, said concentration should be consistent with the means utilized for its dispensation, and should readily permeate the fibrous webs. The resulting product contains between 0.1 to 5% of the hydrophile within the web matrix and successfully negates the anti-wetting effect of the hydrophobic binding agent. Hence, the webs have absorbency rates typically about 20%, but preferably greater than 35% better than their untreated counterparts. Yet, the bulk of the web does not have to be sacrificed to obtain the improvement.

DESCRIPTION OF THE INVENTION

Figure 1:
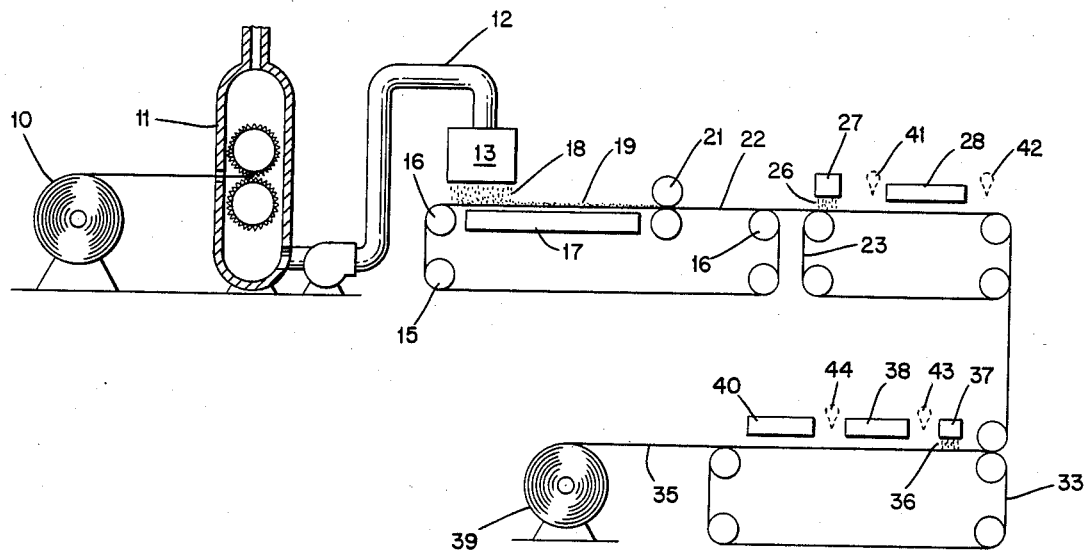
FIG. 1 is a schematic flow diagram of the web forming process.

Referring to FIG. 1, a conventional process flow diagram for air laying dry webs, pulp sheets, laps, or bales 10 are defiberized in defiberizer 11, here a hammermill, and transported pneumatically through line 12 to distributor 13. Various distributor arrangements are well known in the art.

The individual fibers are dispersed onto an endless fourdrinier wire 15, which circles continuously about guide rolls 16. Vacuum means 17 draws and retains the loose fibers 18 onto the wire 15 to form a loose web 19 which has little integrity. The loose web 19 is typically pressed by consolidation rolls 21, which compaction increases web strength sufficient to permit transfer of the pressed web 22 to carrier wire 23. The use of the separate wire 23, which has larger perforations than wire 15 and is made typically from a synthetic plastic material, is less likely to plug with bonding material 26 from dispensing means 27, and is easier to clean. As shown in FIG. 1, in the preferred embodiment of the air laid process the once bonded web is partially dried in dryer 28 and then transferred from the carrier wire 23 to a second carrier wire 33 where a second dispensing means 37 dispenses additional bonding material 36 onto the second surface of the web. While two bonding applications are shown, one application will suffice where the web is porous and has a low basis weight, e.g., less than about 20 lbs. per 3000 sq. ft. ream. Additional information relating to a preferred process for bonding air laid webs is disclosed in U.S. patent application Ser. No. 108,022 filed Dec. 28, 1978 by Pauls et al entitled "Methods of Analyizing Bonding Material Onto Fibrous Webs." After each bonding application, the web is at least partially cured in dryers 28, 38. If the bonding material is not completely cured in dryer 38, a curing oven 40 may be installed as shown in FIG. 1. The web product 35 is finally taken up on a parent roll 39.

The method of the present invention comprises incorporating a soluble hydrophile into the web 22. The hydrophile interacts with binding agent within the matrix to overcome water repellancy. Two competing mechanisms are at work within the web matrix. Capillary attractive forces between the fibers ensure that water will be absorbed. However, capillarity subsumes that the fiber surfaces will be wetted. With the hydrophobic binder coating a substantial percentage of fibers, at least partially, requisite wetting is lessened, and the capillary attractive force reduced. The hydrophile, by also coating portions of fiber, neutralizes the anti-wetting effects of the binder.

Hydrophiles that can be incorporated with the web matrix include crosslinked polyacrylate salts, e.g. Permasorb TM from National Starch, Inc.; acrylate polymers, e.g., Aquakeep TM 10SH from Sumitomo Corporation; cellulose derivatives such as cellulose ethers available under the trademark Aqualon from Hercules, Inc. and hydroxyethyl cellulose manufactured by Union Carbide under the trademark Cellosize, especially hydroxyethyl cellulose compounds having a Brookfield viscosity of between 2500 to 3000 at 25° C. in a 2% by weight water solution, e.g. Cellosize QP100M; poly(vinylpyrrolidones), for example, those manufactured by GAF Corporation under the trademark PVP K, especially PVP K-15, which has an average molecular weight of about 10,000, and PVP K-30, which has an average molecular weight of about 40,000; polyethylene oxides, e.g., Polyox TM WSR N-10 of Union Carbide (molecular weight approximately 100,000); poly(vinyl alcohols) such as Vinol TM 350 manufactured by Air Products Company, which has a viscosity of 55 to 65 cps. at 20° C. (4% solution); glycerins; gelatins, and combinations of same.

The hydrophile can be incorporated into the web matrix downstream of the first application of binder by dispensing means 27, and may be incorporated at one or more application stations 41 to 44 shown in phantom in FIG. 1. That is, the hydrophile may be incorporated after dispensing means 27, after through air dryer 28, after dispensing means 33, after dryer 38, or in one or more of these locations. Preferably, however, the hydrophile is incorporated in stations 42 and 44, to prevent the hydrophobic binder from masking the benefits of the hydrophile inclusion by coating not only the fibers, but the hydrophile as well. Disadvantageously, inclusion of the hydrophile after drier 38 necessitates further drying of the web. While it is within the scope of this invention to incorporate the hydrophile before dispensing means 27, it is realized that the benefit derived thereby is partially negated because the subsequent dispensation of binder will envelop the hydrophile treated fibers to some extent, and may jeopardize the ability of the fibers to bond properly.

The application stations 41 to 44 may be immersion means wherein the web is passed through a bath of the aqueous hydrophile solution. Preferably, the stations are spray means, so that the web does not become overladen with water requiring excessive drying or compaction. Although compaction will itself increase absorbency, it will be at the expense of bulk which is to be maximized.

The hydrophile solution comprises one or more of the aforesaid hydrophile materials in an amount of between about 0.1 to about 10.0% by weight. While the concentration is not particularly critical the solution should have a viscosity such that sufficient solution permeates the web and does not cause clogging of the spray means if such are used. However, the solution should not be so dilute as to unduly wet the web. Preferably, the solution should contain between 1.0 to 5.0% hydrophile by weight.

The amount of hydrophile contained within the web (e.g., hydrophile add on) is between 0.1 to 5.0% by weight of the treated web. The amount of solution required to achieve this level of incorporation may be calculated from the basis weight and web velocity on the wire. Preferably, however, the web product contains between about 0.5 to about 2.5% hydrophile by weight. It is interesting to note that the amount of hydrophile required to negate the effect of the hydrophobic binder is considerably less than the amount of binder applied to the web, the binder accounting for between 10 and 30% of the web basis weight. Hence, the cost of including the hydrophile represents a small fraction of the cost of making the web.

In addition to the above described incorporation methods, the hydrophile may also be included in the binding material emulsion, provided that the concentrations thereof do not compromise the sprayability thereof.

The product web of the present invention has significantly better absorption properties as compared to untreated webs, and is measured by applicant's mirror wipe test. In this test, a given amount of distilled water, 1.4 ml., is placed on a flat 24"×36" mirror. A sheet of given size, 11 inches square, is used to remove the water under hand applied pressure, the time therefor being measured with a stop watch. The time required, mirror wipe time (MWT), is a measure of the absorbency rate of the product. Although this test appears, at first inspection, to be more subjective than mechanical test methods known in the art, applicant, through extensive usage, has found that the test achieves nearly the same degree of precision. More importantly, applicant has found that the test is more indicative of consumer response than the mechanical test procedures. Furthermore, it should be understood that the test is being used to measure gross differences in absorbency rate so that the standard deviations of individual measurements are negligible by comparison.

The table below provides data on air laid handsheets treated by immersion and by spraying using the identified hydrophile solution. Towels treated by immersion were blotted to remove excess liquid; towels of both methods were dried with warm air. The resulting handsheet products were analyzed for hydrophile content and subjected to the mirror wipe test. An untreated handsheet was similarly tested as a control. t,0100

Figure 2:
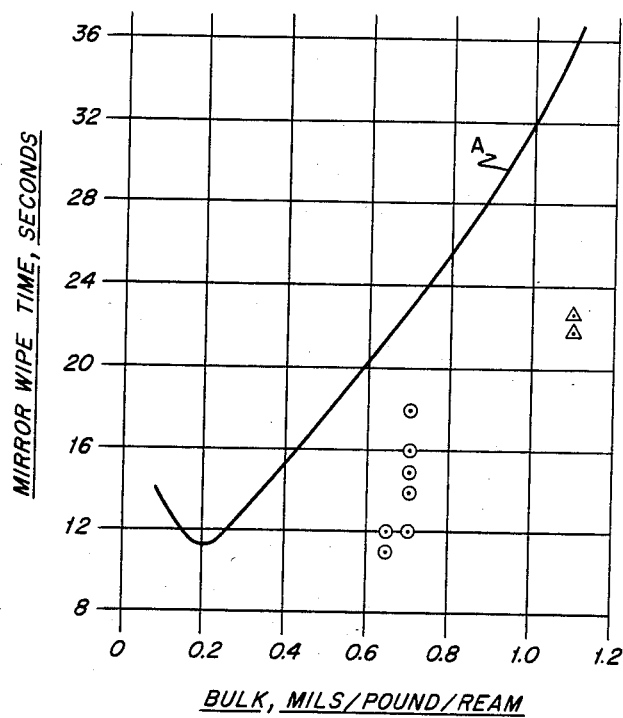
FIG. 2 is a graph illustrating the general relationship between the bulk and absorbency as measured by minimum wipe time for air laid fibrous webs.

FIG. 2 illustrates the general relationship between bulk and MWT for conventional air laid webs (curve A). The data from the table is also plotted in FIG. 2, but without attempt to correlate MWT improvement with the hydrophile species or with the hydrophile add on amount in view of the scatter of the data points. From the graph, it is observed that for untreated webs MWT can be decreased significantly by reducing bulk, the minimum MWT being obtained at a bulk of about 0.2 mil/lb. per ream. Similarly, reduction in bulk for treated webs also reduces MWT, as would be expected. However, at comparative values of bulk, the treated webs provide between about a 20% to a 50% improvement over their untreated counterpart. Spray treatment is particularly preferable when high bulk is required, the webs thus made not requiring pressing to reduce the amount of moisture to be removed by thermal drying means. Conversely, when some reduction in bulk is practicable from a commercial viewpoint the immersion method produces lower MWT's.

The above disclosure is exemplary of the invention, and is not intended to be limiting except as respects the claims which are appended below.

I claim:

1. A process for making an air laid soft. high bulk, absorbent fibrous web having a basis weight in the range between about 8 to about 50 lbs./ream, consisting essentially of the steps of: (a) air laying a loose web; (b) bonding said web with a substantially hydrophobic adhesive material; (c) curing said adhesive material; (d) incorporating into said web an aqueous solution of a water soluble hydrophile at any stage in said process contemporary with or subsequent to said step (b) to enhance the absorbency rate of the web by neutralizing the anti-wetting effects of the substantially hydrophobic adhesive material; and (e) drying said web while retaining between about 0.1 to about 5.0% by weight of said hydrophile, wherein said water soluble hydrophile is selected from the group consisting of polyethylene oxide, cellulose ethers, hydroxymethyl cellulose, polyvinyl alcohol, polyvinyl pyrrolidone, gelatin, graft copolymers of starch, crosslinked polyacrylates, acrylate polymers, crosslinked carboxymethyl cellulose alkali salts, starch or guar gum grafted with acrylamide acid salts in combination with divinyl compounds, glycerin, and compatible combinations thereof.

2. A process for making an air laid soft, high bulk absorbent fibrous web having a basis weight in the range between about 8 to about 50 lbs./ream, comprising the steps of: (a) air laying a loose web; (b) bonding said web with a substantially hydrophobic adhesive material; (c) curing said adhesive material; (d) incorporating into said web an aqueous solution of a water soluble hydrophile at any stage in said process contemporary with or subsequent to said step (b) to enhance the absorbency rate of the web by neutralizing the anti-wetting effects of the substantially hydrophobic adhesive material; and (e) drying said web while retaining between about 0.1 to about 5.0% by weight of said hydrophile, wherein said water soluble hydrophile is selected from the group consisting of polyethylene oxide, cellulose ethers, hydroxymethyl cellulose, polyvinyl alcohol, polyvinyl pyrrolidone, gelatin, graft copolymers of starch, crosslinked polyacrylates, acrylate polymers, crosslinked carboxymethyl cellulose alkali salts, starch or guar gum grafted with acrylamide acid salts in combination with divinyl compounds, glycerin, and compatible combinations thereof.

3. The method of claim 2 wherein the hydrophile material is incorporated within the adhesive material.

4. The method of claim 2 wherein the hydrophile solution is sprayed onto the web, the spray essentially permeating said web.

5. The method of claim 2 wherein the web is immersed in the hydrophile solution.

6. The methods of claim 4 or 5 wherein the web is treated after bonding of the web, the adhesive material being cured in the drying step.

7. The methods of claim 4 or 5 wherein the adhesive material is cured by heating, and the web is then treated with the hydrophile solution and dried.

8. The method of claim 4 wherein each surface of the web is bonded, and one or both surfaces of the web is treated with the hydrophile solution, said web being dried after each hydrophile treatment.

9. The methods of claim 3, 4, 5, or 8 wherein the concentration of the hydrophile in solution is between about 0.1 to about 10% by weight.

10. The methods of claim 9 wherein the absorbency rate is enhanced by at least 20% as compared to untreated webs of similar bulk as measured by mirror wipe time.

11. The methods of claim 10 wherein the amount of the hydrophile preferably retained within the web product is between about 0.5 to about 2.5% by weight.

12. The methods of claim 10 wherein mirror wipe time is less than 18 seconds.

13. The methods of claim 11 wherein the preferred concentration of the hydrophile in solution is between 1.0 to 5.0% by weight.

14. The method of claim 9 wherein the adhesive material is an aqueous latex emulsion.

* * * * *

UNITED STATES PATENT AND TRADEMARK OFFICE
CERTIFICATE OF CORRECTION

PATENT NO. : 4,600,462
DATED      : July 15, 1986
INVENTOR(S) : William R. WATT

Page 1 of 2

It is certified that error appears in the above-identified patent and that said Letters Patent is hereby corrected as shown below:

Column 5, line 10, delete "t,0100".

Column 5, between lines 10 and 11, insert the table attached hereto.

Signed and Sealed this

Sixth Day of November, 1990

Attest:

HARRY F. MANBECK, JR.

*Attesting Officer*  *Commissioner of Patents and Trademarks*

| HYDROPHILE | METHOD APPLICATION | SOLUTION CONCENTRATION (Weight %) | BULK (Mil/lb./ream) | CONCENTRATION OF HYDROPHILE IN WEB (Weight %) | MWT (Secs.) |
|---|---|---|---|---|---|
| Untreated Control | --- | --- | 1.0 | --- | 32 |
| Polyethylene Oxide (Polyox WSR N-10, Union Carbide) | Immersion | 2.0 | 0.7 | 1.2 | 14 |
| Hydroxyethyl Cellulose (Cellosize QP 100M, Union Carbide) | " | 2.0 | 0.7 | --- | 15 |
| Poly(vinyl Alcohol) (Vinol 350, Air Products) | " | 2.0 | 0.7 | --- | 12 |
| Poly(vinylpyrrolidone) (PVP K-30, GAF Corp.) | " | 3.0 | 0.65 | 0.82 | 12 |
| Gelatin | " | 3.0 | 0.70 | 0.75 | 18 |
| Crosslinked Polyacrylate (Permasorb, National Starch) | " | 0.32 | 0.65 | 0.38 | 11 |
| Permasorb | Spray | 0.32 | 1.1 | --- | 23 |
| Permasorb + Aerosol OT | " | 1.0 | 1.1 | 2.68 | 22 |
| Permasorb + 2% Glycerin | Immersion | --- | --- | --- | 10 |